US011717588B2

(12) United States Patent
Yotsumoto et al.

(10) Patent No.: US 11,717,588 B2
(45) Date of Patent: Aug. 8, 2023

(54) DISINFECTION APPARATUS

(71) Applicants: OBAYASHI CORPORATION, Tokyo (JP); OBAYASHI FACILITIES CORPORATION, Tokyo (JP)

(72) Inventors: Mizuyo Yotsumoto, Tokyo (JP); Hiroki Ogata, Tokyo (JP); Satoru Okuda, Tokyo (JP); Yu Suzaki, Tokyo (JP); Yoshio Seishu, Tokyo (JP); Atsuya Yuasa, Tokyo (JP); Sadayoshi Nomizo, Tokyo (JP); Keiichi Tomiki, Tokyo (JP); Hirokazu Suzuki, Tokyo (JP)

(73) Assignees: OBAYASHI CORPORATION, Tokyo (JP); OBAYASHI FACILITIES CORPORATION, Tokyo (JP)

( * ) Notice: Subject to any disclaimer, the term of this patent is extended or adjusted under 35 U.S.C. 154(b) by 527 days.

(21) Appl. No.: 16/653,530

(22) Filed: Oct. 15, 2019

(65) Prior Publication Data
US 2020/0297884 A1    Sep. 24, 2020

(30) Foreign Application Priority Data
Mar. 19, 2019    (JP) .................................. 2019-051647

(51) Int. Cl.
*A61L 2/26*    (2006.01)
*A61L 2/24*    (2006.01)
(52) U.S. Cl.
CPC .................. *A61L 2/26* (2013.01); *A61L 2/24* (2013.01); *A61L 2202/10* (2013.01); *A61L 2209/111* (2013.01); *A61L 2209/134* (2013.01)

(58) Field of Classification Search
CPC .................. A61L 2202/10; A61L 2/24; A61L 2209/134; A61L 2202/122; A61L 2202/15
See application file for complete search history.

(56) References Cited

U.S. PATENT DOCUMENTS

| 2003/0138558 | A1* | 7/2003 | Wang .................... B05B 7/1626 |
| | | | 427/236 |
| 2004/0184950 | A1* | 9/2004 | McVey ..................... F24F 3/16 |
| | | | 422/123 |
| 2011/0305597 | A1* | 12/2011 | Farren ...................... A61L 2/10 |
| | | | 422/24 |

FOREIGN PATENT DOCUMENTS

| JP | 2018-131878 A | 8/2018 |
| JP | 2018131878 A * | 8/2018 |
| WO | WO-2010045619 A1 * | 4/2010 ............... A61L 2/20 |

OTHER PUBLICATIONS

JP 2018131878 A Translation, 2018.*

* cited by examiner

*Primary Examiner* — Kevin Joyner
*Assistant Examiner* — Changru Chen
(74) *Attorney, Agent, or Firm* — Maschoff Brennan

(57) ABSTRACT

A disinfection apparatus includes an installation member. The installation member includes a sealing member configured to seal a hole located in a ceiling, a nozzle configured to be placed in a ceiling space through the hole and spray a chemical solution to disinfect the ceiling space, a mount member configured to place the nozzle above the sealing member, and a fixing member configured to maintain a state in which the sealing member seals the hole.

12 Claims, 5 Drawing Sheets

Fig.1A
Fig.1B
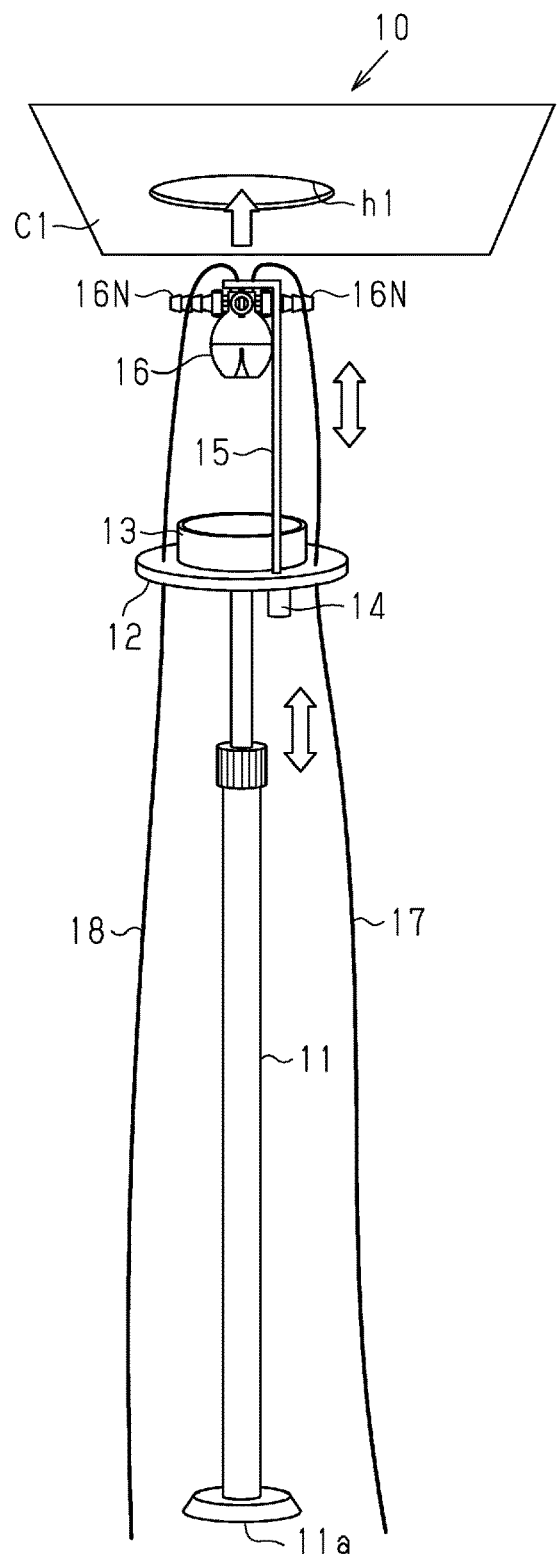
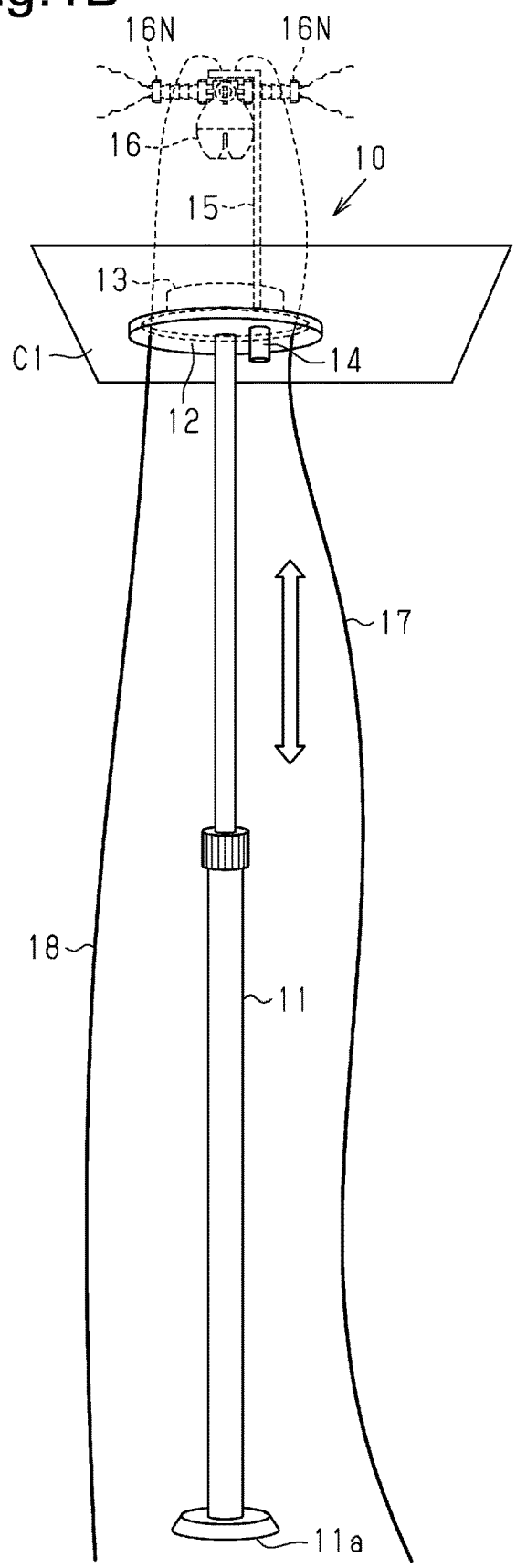

DISINFECTION APPARATUS

BACKGROUND

1. Field

The present disclosure relates to a disinfection apparatus for disinfecting a ceiling space.

2. Description of Related Art

Demolition and repair of a building generate a significant amount of dust, which can contain a large amount of *Aspergillus* spores. In hospitals and elderly facilities, the patients and elderly people with weakened immune systems in these facilities face a high risk of *Aspergillus* infection when inhaling the spores. For this reason, demolition methods have been contemplated that limit spreading of *Aspergillus* fungi during demolition to limit *Aspergillus* infection. See Japanese Laid-Open Patent Publication No. 2018-131878, for example. The demolition method described in this publication uses a disinfection apparatus having a sprayer with a pneumatic atomizing nozzle. The disinfection apparatus is inserted and installed into the ceiling space through an opening. The sprayer sprays mist of a chemical solution for disinfection.

As described in Japanese Laid-Open Patent Publication No. 2018-131878, in order to disinfect by spraying mist of the chemical solution, the mist is sprayed until the humidity in the ceiling space to be disinfected reaches the target relative humidity (for example, 80%). To prevent leakage of the sprayed mist through the opening, the opening used to insert the sprayer into the ceiling space is covered by a plastic sheet, for example. However, covering the opening takes time and trouble, hindering efficient disinfection work.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a disinfection apparatus that includes an installation member is provided. The installation member includes a sealing member configured to seal a hole located in a ceiling, a nozzle configured to be placed in a ceiling space through the hole and spray a chemical solution to disinfect the ceiling space, a mount member configured to place the nozzle above the sealing member, and a fixing member configured to maintain a state in which the sealing member seals the hole.

Other features and aspects will be apparent from the following detailed description, the drawings, and the claims.

BRIEF DESCRIPTION OF THE DRAWINGS

FIG. 1A is a perspective view showing an installation member of a disinfection apparatus of a first embodiment in a state before sealing.

FIG. 1B is a perspective view showing the installation member of the first embodiment.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

This description provides a comprehensive understanding of the methods, apparatuses, and/or systems described. Modifications and equivalents of the methods, apparatuses, and/or systems described are apparent to one of ordinary skill in the art. Sequences of operations are exemplary, and may be changed as apparent to one of ordinary skill in the art, with the exception of operations necessarily occurring in a certain order. Descriptions of functions and constructions that are well known to one of ordinary skill in the art may be omitted.

Exemplary embodiments may have different forms, and are not limited to the examples described. However, the examples described are thorough and complete, and convey the full scope of the disclosure to one of ordinary skill in the art.

First Embodiment

A disinfection apparatus according to a first embodiment will now be described with reference to FIGS. 1A, 1B, and 2. The present embodiment disinfects a ceiling space by spraying a chemical solution having a disinfection effect, which is a solution of active ingredients, in the ceiling space.

FIGS. 1A and 1B show an installation member 10 of a disinfection apparatus.

Figure 2:
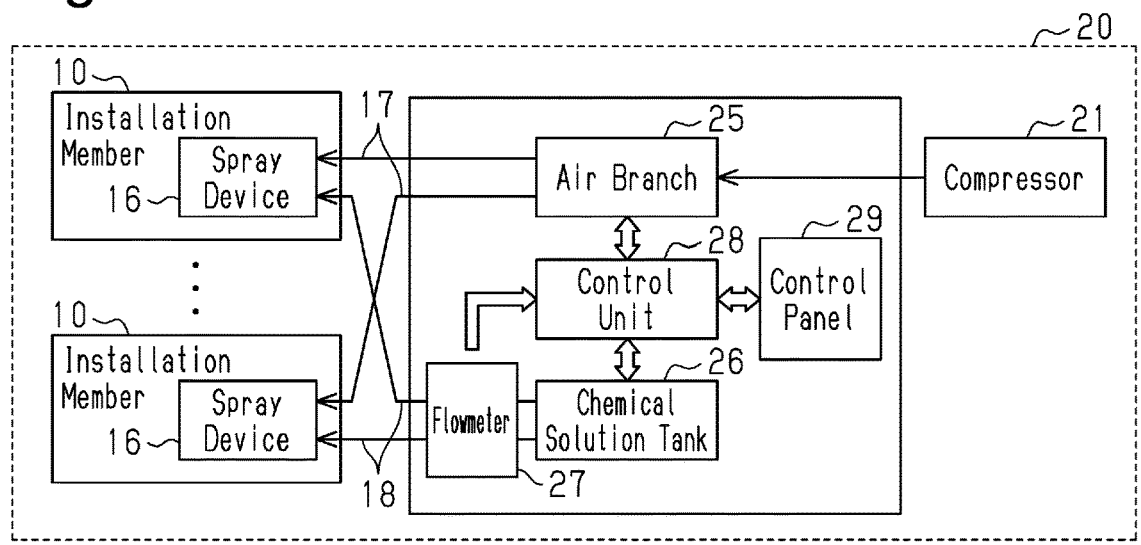
FIG. 2 is a block diagram showing the disinfection apparatus of the first embodiment.

FIG. 2 shows a disinfection apparatus 20 including a plurality of spray devices 16. Each spray device 16 is supported by the corresponding installation member 10 and placed in a ceiling space, that is, a space above a ceiling. The installation member 10 and the spray device 16 will be described in detail below.

The disinfection apparatus 20 includes a compressor 21, an air branch 25, a chemical solution tank 26, flowmeters 27, a control unit 28, and a control panel 29. The compressor 21, which is movable, compresses air and supplies the compressed air to the air branch 25. In the present embodiment, the air branch 25, the chemical solution tank 26, the flowmeters 27, the control unit 28, and the control panel 29 are mounted on a movable cart.

The air branch 25 divides and supplies compressed air to the spray devices 16 via air hoses 17. A pressure gauge (not shown) is provided in the air branch 25 to measure the pressure of the compressed air supplied from the compressor 21.

The chemical solution tank 26 stores a chemical solution for disinfection and supplies the chemical solution to each spray device 16. The present embodiment uses a chemical solution produced by diluting a 6% sodium hypochlorite solution, which is used as liquid concentrate, to 0.3% to 0.5%. The flowmeters 27 are placed at the discharge port of the chemical solution tank 26. Each flowmeter 27 measures the flow rate of the chemical solution supplied to the corresponding spray device 16 via a chemical solution tube 18.

The control unit 28 controls the supply valve (not shown) of the air branch 25 and the supply valve (not shown) of the chemical solution tank to control the supply of the compressed air and the chemical solution to the spray devices 16. The control unit 28 performs various controls in response to instructions received through the control panel 29.

The control panel 29 includes a start button for starting spraying and a timer setting button. In addition, the control panel 29 displays the set time of spraying, the elapsed time from the start of spraying, the integrated flow rate of the chemical solution supplied to each spray device 16, and the pressure of compressed air supplied to the air branch 25, for example.

As shown in FIG. 1A, the installation member 10 includes an extendable support bar 11, which serves as a support. A base 11a is provided at the lower end of the support bar 11 to allow the support bar 11 to stand on the floor. The upper surface of the support bar 11 is fixed to a disk-shaped sealing member 12. In the present embodiment, the center of the sealing member 12 is aligned with the central axis of the support bar 11. In order to seal a circular hole h1 in a ceiling panel C1, the sealing member 12 is larger than this hole h1. The hole h1 is sized to allow the spray device 16 to move through the hole h1.

A vessel 13, which serves as a container, is fixed to the center of the upper surface of the sealing member 12. The vessel 13 is cylindrical and opens upward. The vessel 13 is smaller than the hole h1 in circumference. Further, a drain 14 extends through the vessel 13 and the sealing member 12. The drain 14 includes a drain cock (not shown) at the lower end.

A mount plate 15 extends upright from the sealing member 12. The mount plate 15 of the present embodiment is extendable and retractable according to the height of the ceiling space, and has a length sufficient to place the spray device 16 above any obstacle, such as piping, in the ceiling space (e.g., 80 to 100 cm).

The upper end section of the mount plate 15 extends in the horizontal direction, and the spray device 16 is attached to this upper end section. The spray device 16 includes a tank, which temporarily stores the chemical solution, and a plurality of nozzles 16N, which sprays mist. Each nozzle 16N of the present embodiment is a pneumatic atomizing siphon spray nozzle, which sprays a chemical solution using the pressure of compressed air. Specifically, Quick Fogger (trade name) manufactured by SPRAYING SYSTEMS CO., JAPAN is used as the spray device 16. With this spray device 16, the amount of liquid sprayed from the nozzle 16N per unit time is controllable by changing the pressure of the compressed air. In the present embodiment, the nozzles 16N may be oriented in four directions. Thus, the nozzles may be orientated in selected two directions (e.g., two opposite directions) of the four directions according to an obstacle in the ceiling space. The arranged nozzles spray mist having a particle diameter of 9 to 11 µm.

Each spray device 16 is connected to an air hose 17 and a chemical solution tube 18. The air hose 17 and the chemical solution tube 18 extend through couplers (not shown), which extend through the sealing member 12, to the lower side of the sealing member 12. The air hose 17 is connected to the air branch 25, and the chemical solution tube 18 is connected to the chemical solution tank 26.

[Disinfection Method]

A method for disinfection using the disinfection apparatus is now described.

First, the installation position of the spray device 16 is determined according to the shape and area of the ceiling space to be disinfected. A circular hole h1 is formed in the ceiling panel C1 corresponding to the installation position.

As shown in FIG. 1A, the cart and the compressor 21 are placed near the hole h1, and the support bar 11 of the installation member 10 is placed to stand in a retracted state on the floor directly below the hole h1. The length of the mount plate 15 is adjusted in accordance with the height of the ceiling space in which the spray device 16 is installed.

Then, the support bar 11 is extended, moving the spray device 16 through the hole h1 and inserting the vessel 13 into the hole h1. This brings the sealing member 12 into contact with the lower surface of the ceiling. As shown in FIG. 1B, the sealing member 12 thus seals the hole h1. The support bar 11 is fixed to maintain the length in this state.

All spray devices 16 are installed in the respective target positions by the installation method described above.

Compressed air and the chemical solution are supplied to the spray devices 16 via the air hoses 17 and the chemical solution tubes 18 by activating the compressor 21 and operating the control panel 29. The nozzles 16N of each spray device 16 spray the chemical solution into the ceiling space to perform disinfection. The vessel 13 receives any chemical solution dripped from the spray device 16.

The control unit 28 continues the spraying until the spraying end time, at which the relative humidity in the ceiling space becomes greater than or equal to the target relative humidity (e.g., 80%). The target relative humidity is a humidity capable of killing *Aspergillus* fungi. The spraying end time is determined according to the area (volume) of the ceiling space.

When the spraying end time is reached, the control unit 28 of the disinfection apparatus 20 stops the supply of compressed air and the chemical solution. The disinfection apparatus 20 is left to stand for a predetermined time (e.g., several minutes), and then the drain cock is opened to discharge the chemical solution stored in the vessel 13 through the drain 14. The support bar 11 is retracted to lower the sealing member 12, moving the spray device 16 out of the ceiling space.

The present embodiment has the following advantages.

(1-1) In the present embodiment, each installation member 10 of the disinfection apparatus 20 includes the sealing member 12, to which the spray device 16 is coupled, and the extendable support bar 11, which is coupled to the sealing member 12 at the upper end. The support bar 11 is extended to insert the spray device 16 into the hole h1 of the ceiling panel C1 and to press the sealing member 12 against the ceiling to seal the hole h1. The support bar 11 stands upright in this position, keeping the hole h1 sealed. The installation of the spray device 16 in the ceiling space and the sealing of the hole h1 are achieved in a single series of actions, increasing the efficiency of the disinfection work.

(1-2) The present embodiment includes the vessel 13 fixed to the upper surface of the sealing member 12. The vessel 13 stores the chemical solution dripped from the nozzles 16N of the spray device 16. This reduces the likelihood that the chemical solution drips from the ceiling when the sealing member 12 is removed, for example.

(1-3) The disinfection apparatus 20 of the present embodiment includes a plurality of spray devices 16. Each spray device 16 receives compressed air from the air branch 25 and the chemical solution from the chemical solution tank 26. This allows simultaneous spraying of mist from the plurality of spray devices 16.

(1-4) The present embodiment includes the mount plate 15 coupled to the sealing member 12 to support the spray device 16. The mount plate 15 is long enough to place the spray device 16 above an obstacle, such as piping, in the ceiling space. Consequently, the mist from the nozzles 16N is sprayed efficiently without being interfered by the obstacle.

Second Embodiment

A disinfection apparatus according to a second embodiment will now be described with reference to FIGS. 3A and 3B. The present embodiment disinfects a ceiling space above a system ceiling. The sealing member of the second embodiment is different from that of the first embodiment. In the following description, same reference numerals are given to those components that are the same as the corresponding components of the above embodiment. Such components will not be described in detail.

Figure 3A:
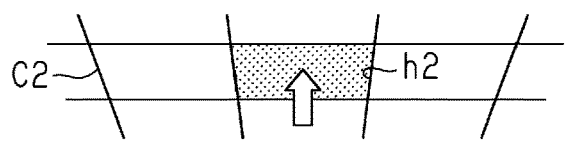
FIG. 3A is a perspective view showing an installation member of a disinfection apparatus of a second embodiment in a state before sealing.
Figure 3B:
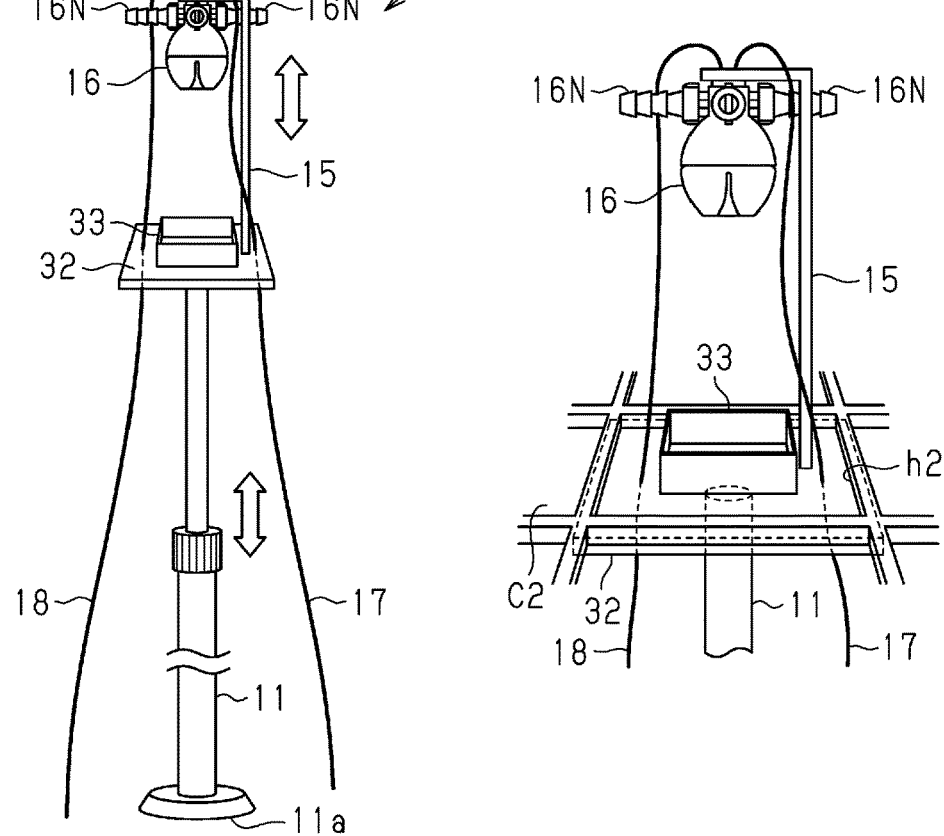
FIG. 3B is a perspective view showing the installation member of the second embodiment in a state after sealing in a ceiling space.

In the present embodiment, as shown in FIG. 3A, a system ceiling is formed by arranging ceiling joists, which may be T-bars, in a grid and covering each of the spaces surrounded by the grid ceiling joists with a ceiling panel C2. The grid of the ceiling joists may include 450 mm squares, 600 mm squares, or 600 mm×1200 mm rectangles, for examples.

The installation member 30 of the present embodiment includes an extendable support bar 11, a sealing member 32, a mount plate 15, and a spray device 16. The sealing member 32 is a tetragonal panel having substantially the same size as the ceiling panel C2. The sealing member 32 seals a hole surrounded by the grid ceiling joists. A vessel 33, having the shape of a tetragonal frame, is arranged on the sealing member 32. The vessel 33 is sized to be inserted into the hole surrounded by the grid ceiling joists.

This embodiment uses the same disinfection steps as the embodiment described above. The ceiling panel C2 corresponding to the position in which the spray device 16 is installed is removed to form a hole h2 connecting to the ceiling space.

Then, the support bar 11 of the installation member 30 is placed upright on the floor directly below the hole h2. The support bar 11 is extended to elevate the spray device 16 and the sealing member 32. As shown in FIG. 3B, this moves the spray device 16 through the hole h2 and brings the sealing member 32 into contact with the lower surface of the ceiling joists, thereby sealing the hole h2. Then, the compressor 21 is activated to spray the chemical solution from the nozzles 16N of the spray device 16 to perform disinfection.

In addition to Advantages (1-1) to (1-4) described above, the present embodiment has the following advantage.

(2-1) In the present embodiment, the installation member 30 of the disinfection apparatus 20 includes the sealing member 32 having a shape corresponding to the grid of the grid ceiling. This achieves efficient disinfection of the ceiling space above the grid ceiling without forming a hole in the ceiling.

Third Embodiment

A disinfection apparatus according to a third embodiment will now be described with reference to FIGS. 4A to 4C. The first and second embodiments seal the holes with the sealing members supported by the extendable support bars 11. The present embodiment inserts a spray device into a ceiling space through an access opening formed in the ceiling. The installation member is hooked to the frame surrounding the access opening to seal the access opening.

Figure 4A:
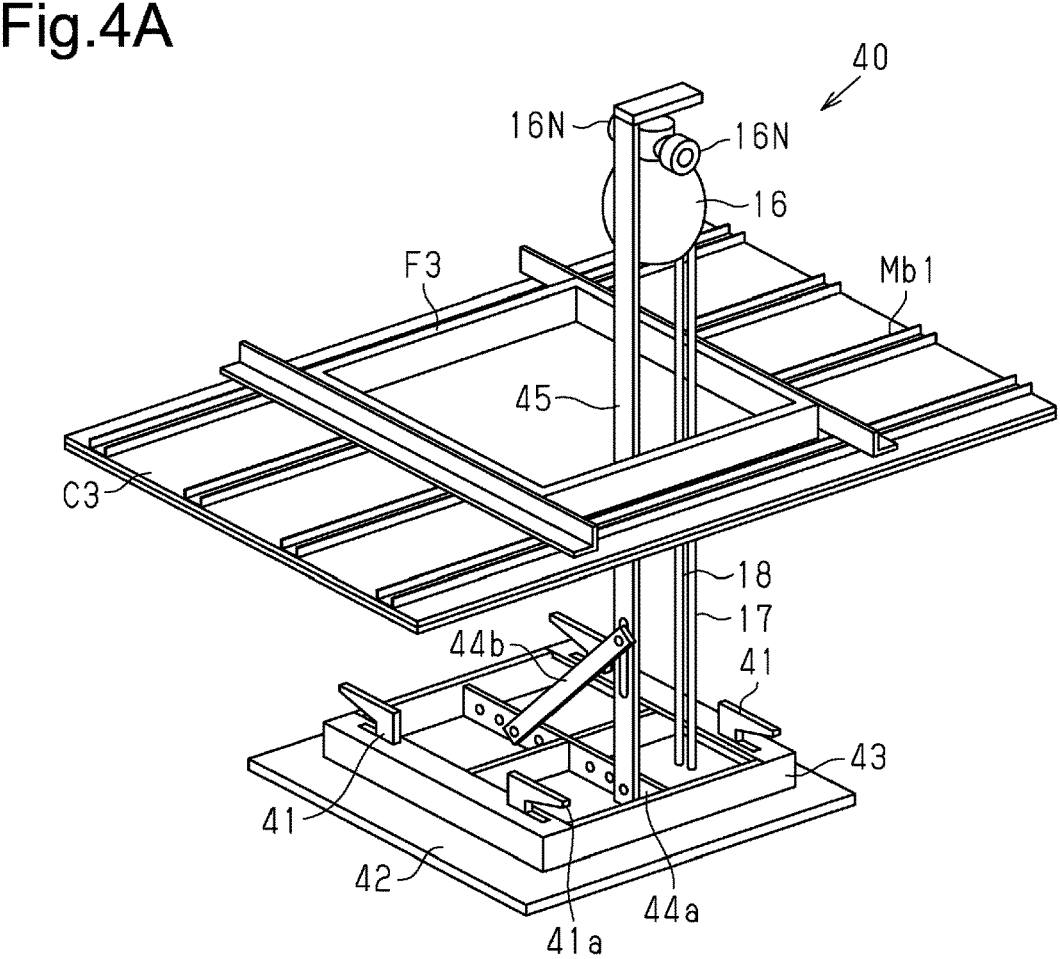
FIG. 4A is a perspective view showing an installation member of a disinfection apparatus of a third embodiment in a state before sealing.

As shown in FIG. 4A, an access opening frame F3 having the shape of a tetragonal frame is arranged in the ceiling space around the periphery of the access opening. In addition, a plurality of ceiling joists Mb1 is arranged on the ceiling panel C3 in the ceiling space.

An installation member 40 includes a plurality of slide hooks 41, which serves as fixing members (engagement portions), a sealing member 42, and an insertion portion 43. The sealing member 42 is large enough to cover the access opening. The insertion portion 43 is arranged on the central section of the sealing member 42. The insertion portion 43 has the shape of a tetragonal frame sized to be inserted into the access opening. The insertion portion 43 has four through holes, each receiving a slide hook 41, which can slide in the horizontal direction in the through hole. In the present embodiment, the four slide hooks 41 include two pairs of slide hooks 41. The two slide hooks 41 in each pair are spaced apart from each other along one straight line.

Figure 4B:
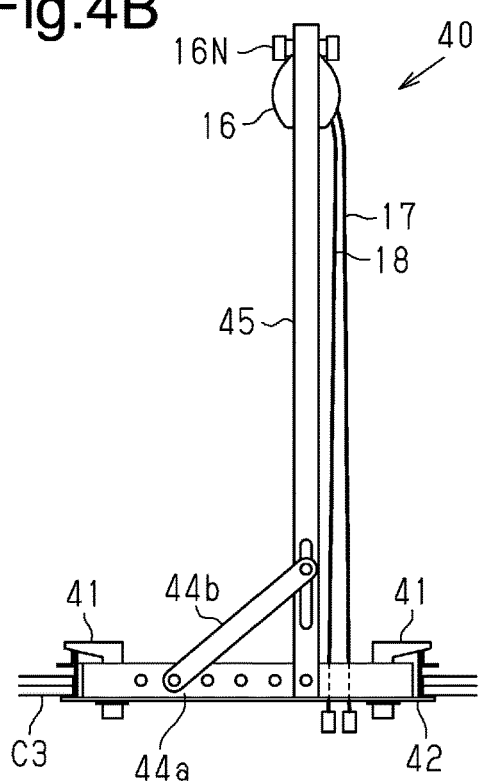
FIG. 4B is a front view showing the installation member of the disinfection apparatus of the third embodiment in a state after sealing.

As shown in FIGS. 4A and 4B, a mount member 44a is located in the region surrounded by the insertion portion 43 on the upper surface of the sealing member 42. The insertion portion 43 functions as a container for receiving dripped chemical solution. The mount member 44a includes a plurality of coupling holes arranged in the lateral direction. The lower end of a stay 44b and the lower end of a mount plate 45 are fixed to the mount member 44a by fasteners, such as bolts and nuts. The upper end of the stay 44b is coupled to the central section of the mount plate 45 to support the mount plate 45. The mount plate 45 is the same as the mount plate 15 of the first embodiment.

The spray device 16 is attached to the upper end of the mount plate 45. The air hose 17 and the chemical solution tube 18 connected to the spray device 16 extend through the sealing member 42.

Figure 4C:
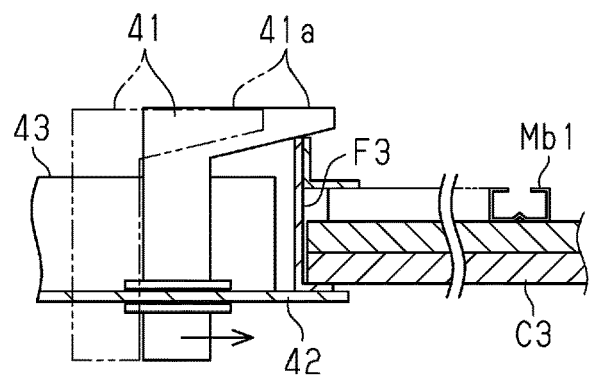
FIG. 4C is an enlarged side view showing the main part of the installation member of the disinfection apparatus of the third embodiment in a state after sealing.

As shown in FIG. 4C, each slide hook 41 is substantially an inverted L-shaped plate including a projection 41a at the upper end. The projection 41a extends toward the outside of the installation member 40. The lower surface of the projection 41a is inclined so as to be higher toward the outside of the installation member 40. The lower surface of the projection 41a is high enough to be hooked onto the upper end of the access opening frame F3.

The lower end of the slide hook 41 extends through the sealing member 42 and protrudes from the lower surface of the sealing member 42. The lower end is slidable along the insertion portion 43.

In the present embodiment, to perform disinfection, the access door covering the access opening is removed, and the cart and the compressor 21 are placed near the access opening.

Coupling holes are selected according to the installation position of the spray device 16, and the mount plate 45 and the stay 44b are engaged with and fixed to these coupling holes with fasteners. The mount plate 45 and the stay 44b are thus fixed.

As shown in FIG. 4A, the installation member 40 is placed directly below the access opening.

Then, as shown in FIG. 4B, the installation member 40 is lifted to place the spray device 16 in the ceiling space through the access opening, and the sealing member 42 is brought into contact with the lower surface of the ceiling panel C3.

As shown in FIG. 4C, with the sealing member 42 in contact with the lower surface of the ceiling panel C3, the lower ends of the slide hooks 41 are moved so that the sealing member 42 engages with the upper end of the access opening frame F3. Thus, the spray device 16 is installed in the ceiling space, and the installation member 40 is fixed to the access opening frame F3 with the sealing member 42 sealing the access opening. The compressor 21 is then activated to spray the chemical solution from the nozzles 16N of the spray device 16 to perform disinfection. The insertion portion 43 receives any chemical solution dripped from the spray device 16.

In addition to advantages equivalent to (1-3) and (1-4), the present embodiment has the following advantage.

(3-1) The installation member 40 of the present embodiment includes the sealing member 42, which is coupled to the spray device 16, and a plurality of slide hooks 41, which is arranged in the insertion portion 43 of the sealing member 42 in a slidable manner. This allows the slide hooks 41 to engage with the upper surface of the access opening frame F3, thereby installing the spray device 16 in the ceiling space and maintaining a state in which the sealing member 42 seals the access opening.

(3-2) In the present embodiment, each slide hook 41 includes an upper projection 41a, and the lower surface of the projection 41a is inclined. This allows the slide hook 41 to be moved into engagement with the access opening frame F3.

(3-3) The present embodiment includes the mount member 44a, which has a plurality of coupling holes and is located on the sealing member 42 of the installation member 40. The mount member 44a is coupled with the mount plate 45, to which the spray device 16 is attached, and the stay 44b, which is connected to the mount plate 45. Thus, the position where the mount plate 45 is coupled to a coupling hole is adjustable.

(3-4) The present embodiment includes the insertion portion 43 fixed to the upper surface of the sealing member 42. Any chemical solution dripped from the nozzles 16N is stored inside this insertion portion 43, reducing the likelihood that the chemical solution drips from the ceiling when the sealing member 42 is removed, for example.

Fourth Embodiment

A disinfection apparatus according to a fourth embodiment will now be described with reference to FIGS. 5A to 5D. In the third embodiment, the spray device 16 is attached to the upper end of the mount plate 45 of the installation member 40, and the installation member 40 is fixed with the slide hooks 41. In the present embodiment, only the nozzles of the spray device are attached to the mount plate, and disinfection is performed without removing the access door.

Figure 5A:
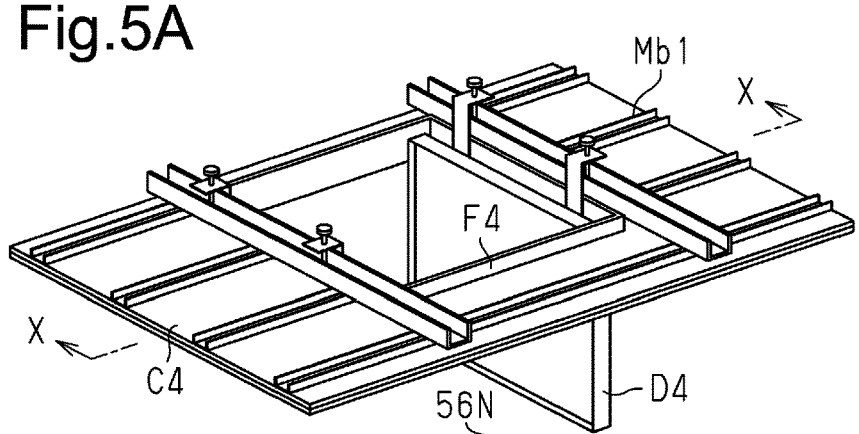
FIG. 5A is a partially exploded perspective view showing an installation member of a disinfection apparatus of a fourth embodiment in a state before sealing.
Figure 5B:
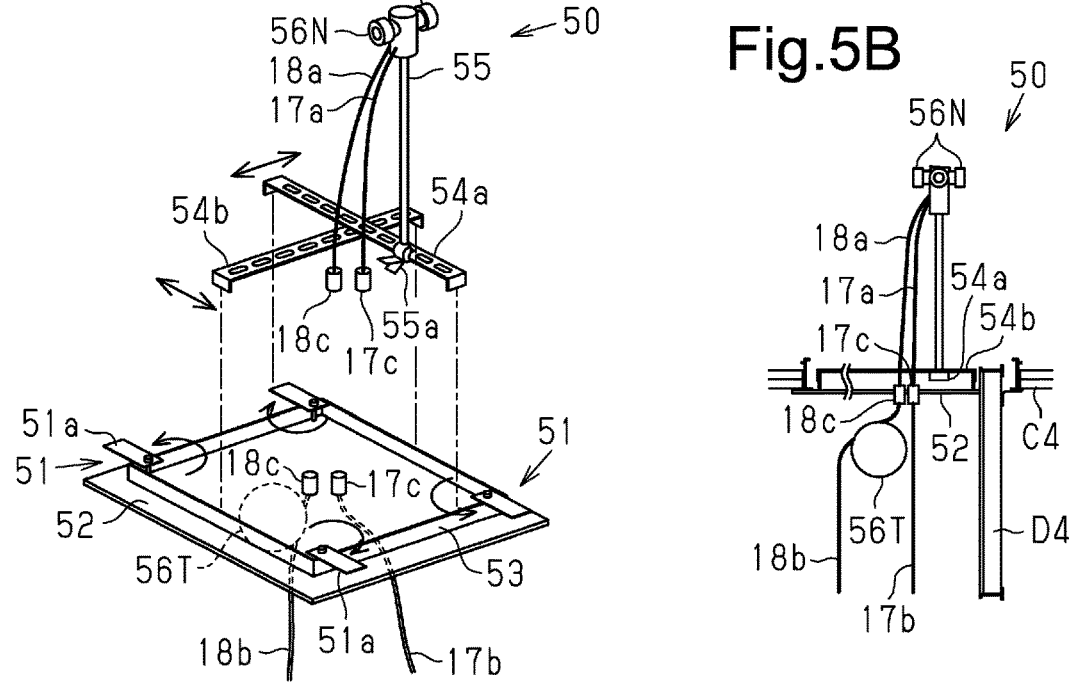
FIG. 5B is a front view showing the installation member of the disinfection apparatus of the fourth embodiment in a state after sealing.
Figure 5C:
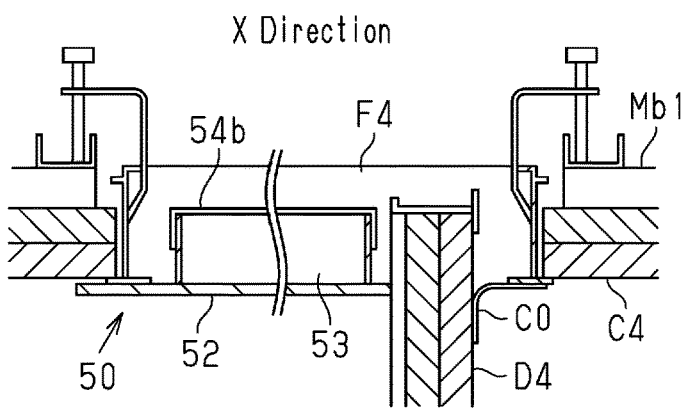
FIG. 5C is a front cross-sectional view showing the main part of the installation member of the disinfection apparatus of the fourth embodiment in a state after sealing.
Figure 5D:
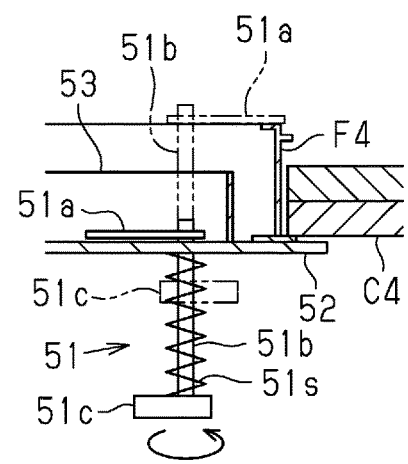
FIG. 5D is an enlarged side cross-sectional view showing the main part of the installation member of the disinfection apparatus of the fourth embodiment in a state after sealing.

FIG. 5A is a partially exploded perspective view of an installation member 50 of the present embodiment. FIG. 5B is a schematic front view of the installation member 50. FIG. 5C is an enlarged cross-sectional front view partially showing the main part of the installation member 50. FIG. 5D is an enlarged cross-sectional side view partially showing the main part of the installation member 50.

As shown in FIGS. 5A and 5B, an access opening frame F4, which has the shape of a tetragonal frame, is placed in a ceiling space around the periphery of an access opening formed in a ceiling. An access door D4 is attached using an engagement member so as to open and close the access opening.

The installation member 50 of the present embodiment includes a plurality of fixing members 51, a sealing member 52, and an insertion portion 53. The fixing members 51 will be described in detail below.

As shown in FIG. 5C, the sealing member 52 is sized to cover the region of the access opening when the access door D4 is opened. On the central section of the sealing member 52, the planar insertion portion 53 extends upright to form a rectangular frame. The insertion portion 53 functions as a container for receiving dripped chemical solution.

As shown in FIG. 5A, a fixing member 51 is placed at each corner of the insertion portion 53. Further, as shown in FIGS. 5A and 5B, a spray tank 56T is placed under the sealing member 52. The spray tank 56T is a part of the spray device separated from the nozzles 56N.

As shown in FIGS. 5B and 5C, support bases 54a and 54b are arranged to intersect with each other in the region of the upper surface of the sealing member 52 surrounded by the insertion portion 53. The long dashed short dashed lines in FIG. 5A indicate the positions along the outer shape of the insertion portion 53 at which the support bases 54a and 54b engage. The two ends of each of the support bases 54a and 54b are bent downward and fitted to the outer side of the insertion portion 53. The support bases 54a and 54b have a plurality of engagement holes. The arrangement of the support bases 54a and 54b in the installation member 40 is changeable by adjusting positions of the engagement holes of the support bases 54a and 54b when the support bases 54a and 54b are brought into engagement. An extendable mount plate 55 extends upright from the support base 54a. A fixing clip 55a is fixed to the lower end of the mount plate 55. In the present embodiment, the fixing clip 55a is attached to the support base 54a. The mount plate 55 is the same as the mount plate 15 of the first embodiment.

A plurality of nozzles 56N is attached to the upper end of the mount plate 55 in a rotational manner. The plurality of nozzles 56N sprays mist in opposite directions along a straight line. The nozzles 56N are a part of the spray device 16 separated from the spray tank 56T.

As shown in FIG. 5B, an air hose 17a and a chemical solution tube 18a are connected to the nozzles 56N. The air hose 17a is connected to the compressor 21 via a coupler 17c, which is provided in the sealing member 52, and an air hose 17b. The chemical solution tube 18a is connected to the spray tank 56T via a coupler 18c provided in the sealing member 52. The spray tank 56T is connected to the chemical solution tank 26 via a chemical solution tube 18b.

Referring to FIG. 5D, the fixing members 51 are now described in detail.

Each fixing member 51 includes a hook plate 51a at the upper end, a handle 51c at the lower end, and a shaft 51b fixed to the hook plate 51a and an end of the handle 51c. The hook plate 51a is an engagement portion having a length extending to the access opening frame F4. The shaft 51b extends through the sealing member 52 at the inner side of the corresponding corner of the insertion portion 53. The shaft 51b has a length greater than the height of the access opening frame F4. A spring 51s is arranged along the section of the shaft 51b between the lower surface of the sealing member 52 and the upper surface of the handle 51c.

To perform disinfection, the cart and the compressor 21 are set, and the access door covering the access opening is opened. Then, as shown in FIG. 5A, the support bases 54a and 54b are engaged with the upper end of the insertion portion 53, and the fixing clip 55a of the mount plate 55 is attached to the support base 54a to set the nozzles 56N on the installation member 50. According to the installation position of the nozzles 56N, the support bases 54a and 54b may be moved along the upper end of the insertion portion 53.

Then, the installation member 50 is lifted so that the nozzles 56N are placed in the ceiling space through the access opening, inserting the insertion portion 53 of the installation member 50 into the access opening. As shown in FIG. 5C, the installation member 50 is further lifted to bring the sealing member 52 into contact with the lower surface of the ceiling panel C4.

With the sealing member 52 in contact with the lower surface of the ceiling panel C4, the handle 51c of each fixing member 51, which is indicated by a solid line in FIG. 5D, is held to press the fixing member 51 upward, compressing the spring 51s. As indicated by the long dashed double-short dashed lines in FIG. 5D, the hook plate 51a is rotated by rotating the handle 51c and engaged with the upper end of the access opening frame F4. The restoring force of the spring 51s draws the hook plate 51a downward, thereby fixing the hook plate 51a to the access opening frame F4. As a result, the nozzles 56N are installed in the ceiling space, and the installation member 50 is fixed to the access opening frame F4 with the sealing member 52 sealing the access opening.

Further, as shown in FIG. 5C, a sheet member C0 or a rubber member covers a section of the access door D4 and a section of the ceiling near the engagement member of the access door D4. Then, the compressor 21 is activated to spray the chemical solution from the nozzles 56N to perform disinfection. Any chemical solution dripped from the nozzles 56N is stored inside the insertion portion 53.

In addition to advantages equivalent to (1-3), (1-4), and (3-4), the present embodiment has the following advantage.

(4-1) In the present embodiment, the installation member 50 includes the sealing member 52, which is coupled with the nozzles 56N for spraying mist, and the fixing members 51 attached to the sealing member 52. Each fixing member 51 includes a hook plate 51a at the upper end of the shaft 51b. The fixing member 51 is pressed upward and rotated to engage the hook plate 51a with the upper surface of the access opening frame F4. This installs the nozzles 56N in the ceiling space and maintains the state in which the sealing member 52 seals the access opening.

(4-2) In the present embodiment, the installation member 50 is fixed to the access opening frame F4 without removing the access door D4. The sealing member 52 thus seals the access opening with the access door D4 attached.

(4-3) In the present embodiment, the nozzles 56N, which are separated from the spray tank 56T, are attached to the mount plate 55 extending upright from the sealing member 52 of the installation member 50. As such, even when the ceiling space has a narrow clearance due to an obstacle such as piping, the nozzles 56N can be placed in the narrow clearance to spray mist.

Fifth Embodiment

A disinfection apparatus according to a fifth embodiment will now be described with reference to FIGS. 2 and 6A to 6C. In the fourth embodiment described above, the mount plate to which only the nozzles of the spray device are attached is coupled to the sealing member. The present embodiment includes a nozzle installation member including a mount plate to which only the nozzles of the spray device are attached. The nozzle installation member is coupled separately from the sealing member. In a similar manner as the fourth embodiment, the present embodiment performs disinfection without removing the access door.

Figure 6A:
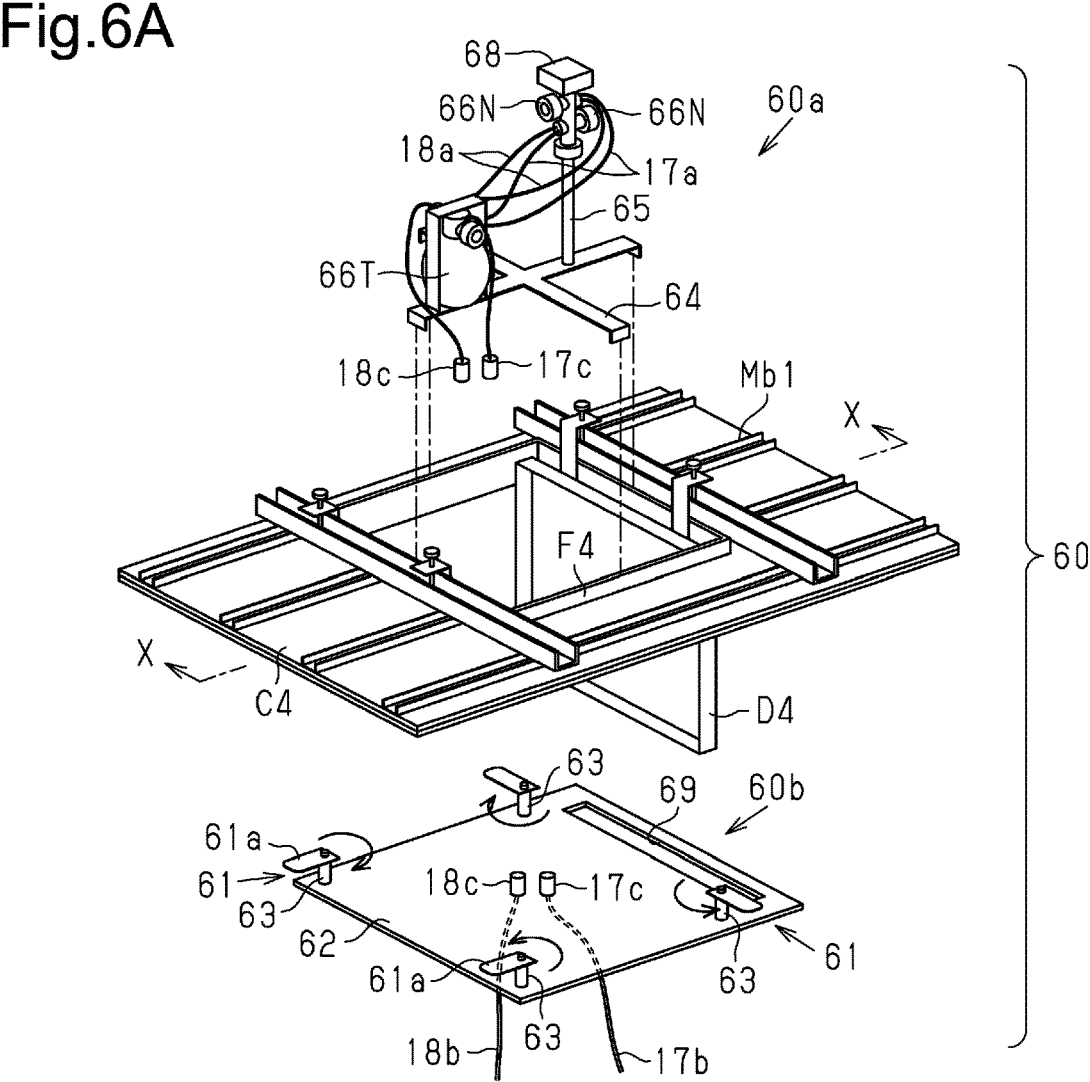
FIG. 6A is a partially exploded perspective view showing an installation member of a disinfection apparatus of a fifth embodiment.
Figure 6B:
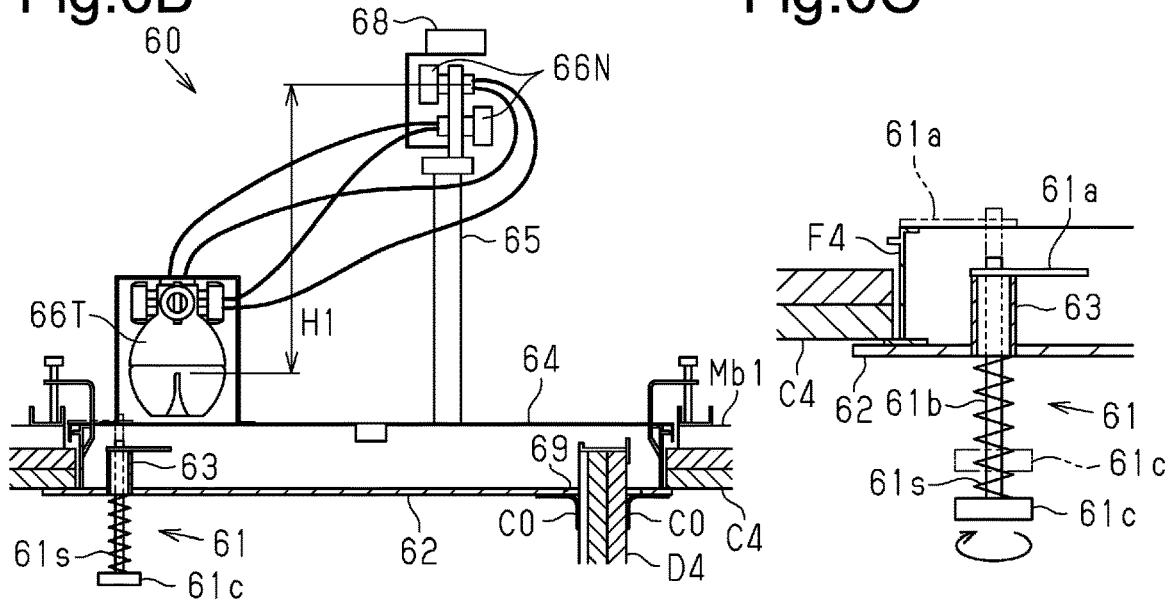
FIG. 6B is a front view showing the installation member of the disinfection apparatus of the fifth embodiment in a state after sealing.
Figure 6C:
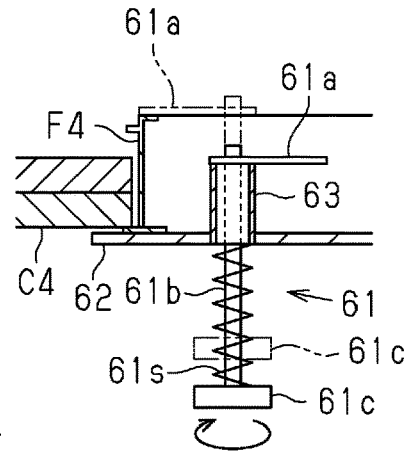
FIG. 6C is an enlarged side cross-sectional view showing the main part of the installation member of the disinfection apparatus of the fifth embodiment in a state after sealing.

FIG. 6A is an exploded perspective view in which an installation member 60 of the present embodiment is partially exploded. FIG. 6B is a schematic front view showing the installation member 60 in a state after sealing. FIG. 6C is an enlarged cross-sectional side view partially showing the main part of the installation member 60.

The installation member 60 of the present embodiment includes a nozzle installation member 60a and a seal installation member 60b. The nozzle installation member 60a and the seal installation member 60b are separate members, which are attached to an access opening frame F4 separately.

The nozzle installation member 60a includes a cross-shaped support base 64 made of a magnetic material. The four ends of the support base 64 are bent downward and fit to the outer side of the access opening frame F4. A spray tank 66T is fixed on the support base 64. The air hose and the chemical solution tube connected to the spray tank 66T extend through the sealing member 62 of the seal installation member 60b via couplers 17c and 18c and are connected to the air branch and the chemical solution tank.

Further, a mount bar 65 is fixed to the support base 64. A neodymium magnet is provided at the bottom of the mount bar 65. The magnetic force allows the mount bar 65 to stand stably at a desired position on the support base 64.

As shown in FIGS. 6A and 6B, multiple (two) nozzles 66N are rotationally attached to the upper end section of the mount bar 65 at different positions in the up-down direction. The nozzles 66N are a part of the spray device 16 separated from the spray tank 66T. The nozzles 66N are rotated to spray mist in desired directions. The nozzles 66N are supported by the support base 64 and the mount bar 65. Each nozzle 66N is connected to an air hose 17a and a chemical solution tube 18a and receives compressed air and the chemical solution from the spray tank 66T. In the present embodiment, the height H1 of each nozzle 66N (the upper nozzle 66N in this example) from the liquid surface in the spray tank 66T is set to be less than or equal to a predetermined height that does not affect the amount of sprayed mist (e.g., 30 cm).

A hygrometer 68 is located above the nozzles. The hygrometer 68 is attached to the mount bar 65 via a rotational mount member.

The hygrometer 68 of the present embodiment is connected to the control unit 28 shown in FIG. 2 and sends the measured humidity (the measurement value) to the control unit 28. Further, in the present embodiment, the control panel 29 includes an automatic stop button for stopping the spraying when the humidity reaches the target relative humidity. When the automatic stop button is selected, the control unit 28 periodically determines whether the humidity obtained from the hygrometer 68 has reached the target relative humidity. When the humidity reaches the target relative humidity, the control unit 28 stops the spraying from the nozzles 66N.

The seal installation member 60b includes a plurality of fixing members 61, a sealing member 62, and a plurality of tubular members 63.

The sealing member 62 is a rectangular panel and large enough to cover the access opening. The sealing member 62 includes an opening 69 in one edge section. The opening 69 is configured to receive the access door D4. The four tubular members 63 are fixed to the upper surface of the sealing member 62. The tubular members 63 extend upright from the sealing member 62 at positions near the corners so as to be placed within the access opening. The height of the upper surfaces of the tubular members 63 is slightly less than the height of the access opening frame F4.

As shown in FIG. 6C, in a similar manner as the fixing members 51 of the fourth embodiment, each fixing member 61 includes a hook plate 61*a*, a handle 61*c*, and a shaft 61*b*. The hook plate 61*a* is an engagement portion, which is located at the upper end of the shaft 61*b* and has a length extending to the access opening frame F4. When the hook plate 61*a* is not in engagement with the access opening frame F4, the hook plate 61*a* engages with the upper surface of the tubular member 63. The handle 61*c* is located at the lower end of the shaft 61*b*. The shaft 61*b* extends through the sealing member 62 and the tubular member 63 and has a length greater than the height of the access opening frame F4. A spring 61*s* is arranged along the section of the shaft 61*b* between the lower surface of the sealing member 62 and the upper surface of the handle 61*c*.

In the present embodiment, to perform disinfection, the cart and the compressor 21 are set, and the access door is opened. As shown in FIG. 6A, the support base 64, to which the spray tank 66T is fixed in advance, is tilted and inserted through the access opening, and the ends of the support base 64 are hooked onto the upper end of the access opening frame F4. The mount bar 65, to which the nozzle 66N and the hygrometer 68 are attached, is fixed to the support base 64 with its position adjusted to avoid obstacles in the ceiling space. The length of the mount bar 65 is adjusted to complete the installation of the nozzle installation member 60*a* in the ceiling space.

Then, the coupler 17*c* of the air tube and the coupler 18*c* of the chemical solution tube, which are connected to the spray tank 66T, are connected to the corresponding couplers 17*c* and 18*c* of the sealing member 62. The seal installation member 60*b* is lifted such that the access door D4 is inserted into the opening 69 of the sealing member 62, and the sealing member 62 is brought into contact with the lower surface of the ceiling panel C4.

In this state, each handle 61*c* is held to press the fixing member 61 upward while compressing the spring 61*s* so that the hook plate 61*a* is located above the upper surface of the access opening frame F4. As indicated by the long dashed double-short dashed lines in FIG. 6C, the hook plate 61*a* is rotated by rotating the handle 61*c* and engaged with the upper end of the access opening frame F4. Thus, the seal installation member 60*b* is fixed, and the sealing member 62 seals the access opening under the nozzle installation member 60*a*. A sheet member C0 (or a rubber member) fixed in advance around the opening 69 closes the gap between the opening 69 of the sealing member 62 and the access door D4. Then, the compressor 21 is activated to spray the chemical solution from the nozzles 66N to perform disinfection.

In addition to advantages equivalent to (1-3), (4-1), and (4-2), the present embodiment has the following advantage.

(5-1) The installation member 60 of the present embodiment includes the nozzle installation member 60*a*, which includes the support base 64 to which the nozzles 66N are fixed, and the seal installation member 60*b*, which includes the sealing member 62 and is separated from the nozzle installation member 60*a*. This allows the nozzles 66N to be set on the access opening frame F4 separately from the sealing member 62 before the installation of the sealing member 62. Thus, the position of the nozzles 66N is adjustable separately from the sealing member 62.

(5-2) The nozzles 66N of the present embodiment are arranged in two upper and lower tiers, and an air hose 17*a* and a chemical solution tube 18*a* are connected to each nozzle 66N. The air hose 17*a* and the chemical solution tube 18*a* are therefore unlikely to hinder the adjustment of the orientation of the nozzle 66N, allowing the compressed air and the chemical solution to be smoothly supplied to each nozzle 66N.

(5-3) The height H1 of each nozzle 66N of the present embodiment from the liquid surface in the spray tank 66T is set to be less than or equal to a predetermined height that does not affect the amount of sprayed mist. The amount of sprayed mist decreases as the height of the nozzle 66N from the liquid surface in the spray tank 66T increases. Thus, setting the height of the nozzle 66N to be less than or equal to the predetermined height limits decrease in the amount of sprayed mist.

(5-4) In the present embodiment, the shaft 61*b* of each fixing member 61 extends through the tubular member 63 projecting from the sealing member 62, and the upper surface of the tubular member 63 supports the hook plate 61*a*. Thus, the fixing of the sealing member 62 is achieved by pressing and moving each fixing member 61 upward only by the distance between the tubular member 63 and the access opening frame F4 and rotating the fixing member 61.

(5-5) The present embodiment includes the hygrometer 68 located above the nozzles 66N. This allows the hygrometer 68 to be set in the ceiling space simultaneously with the installation of the nozzles 66N.

(5-6) In the present embodiment, when the automatic stop button is selected, the control unit 28 stops the spraying from the nozzles 66N when the humidity measured by the hygrometer 68 reaches the target relative humidity. The present embodiment stops the spraying when the hygrometer detects that the humidity necessary for disinfection is achieved, allowing for the efficient spraying of the chemical solution.

The above-described embodiments may be modified as follows. The above-described embodiments and the following modifications can be combined as long as the combined modifications remain technically consistent with each other.

In the first to fourth embodiments, the spray device 16 or the nozzles 56N are attached to the mount plate that is long enough to place the spray device 16 above an obstacle, such as piping, in the ceiling space. However, the spray device 16 or the nozzles 56N may be supported by the installation member using a shorter mount plate. Further, the spray device 16 or the nozzles 56N may be supported by a mount plate coupled to the sealing member via a mechanism that allows switching between different types of mount plates.

In the third to fifth embodiments, the spray device 16 or the nozzles 56N, 66N are placed in the ceiling space through the access opening, and the installation members 40, 50 and 60 engage with the access opening frames F3 and F4 to seal the access openings with the sealing members 42, 52 and 62. The members that are brought into engagement to maintain the sealing member in a sealing state is not limited to the access opening frames F3 and F4 and may be the access door or other ceiling access opening components, which form the ceiling access opening, or ceiling components, which form the ceiling. The ceiling components include the ceiling panel C1 with the hole h1 of the first embodiment and the grid ceiling of the second embodiment. For the grid ceiling, the grid of the grid ceiling may be brought into engagement to maintain the sealing member in a sealing state.

The third embodiment uses the slide hooks 41 to fix the installation member 40 to the access opening frame F3. In the fourth and fifth embodiments, the installation members 50 and 60 are fixed to the access opening frames F4 using the fixing members 51 and 61. The structure for fixing the installation member to a ceiling access opening component or a ceiling component is not limited to the fixing members 51 or 61. For example, the installation members (40, 50 and 60) of the third to fifth embodiments may be placed on a ceiling panel with a hole or on the grid ceiling joists. Further, the installation member may be fixed to the ceiling joists Mb1 in the ceiling space.

In the third to fifth embodiments, the slide hooks 41 and the fixing members 51 and 61 engage with the access opening frames F3 and F4 to fix the sealing members 42, 52 and 62 so as to seal the access opening. However, instead of the slide hooks 41 and the fixing members 51 and 61, the support bar 11 of the first and second embodiments may be used to maintain a state in which the sealing member seals the access opening. Further, the support of the installation member is not limited to the support bar 11, and may be a jack, for example.

The third embodiment removes the access door to set the installation member 40, whereas the fourth and fifth embodiments set the installation members 50 and 60 without removing the access door D4. In the third embodiment, the sealing member may be set without removing the access door. In the fourth and fifth embodiments, the access door D4 may be removed to set the sealing member.

The first to third embodiments set the spray devices 16 in the ceiling space, whereas the fourth and fifth embodiments set the nozzles 56N and 66N, which are separated from the spray tanks 56T and 66T, in the ceiling space. As long as the chemical solution is sprayed in the ceiling space, the tanks may be separated from the nozzles also in the first to third embodiments.

The fourth embodiment sets the nozzles 56N above the sealing member 52 and sets the spray tank 56T under the sealing member 52. However, as with the fifth embodiment, the fourth embodiment may have a configuration that limits decrease in the amount of sprayed mist by setting the height of the nozzles 56N from the liquid surface in the spray tank 56T to be less than or equal to a predetermined height that does not affect the amount of sprayed mist.

The fifth embodiment has a plurality of tubular members 63 extending upright from the upper surface of the sealing member 62. In addition, a container for receiving dripped chemical solution may be arranged on the center of the upper surface of the sealing member 62. In this case, a container with a height lower than the access opening frame F4 may be used to avoid contact with the support base 64 attached to the access opening frame F4, or a plurality of containers may be arranged avoiding the support base 64.

The installation member 60 of the fifth embodiment includes the hygrometer 68 located above the nozzles 66N to measure the humidity in the ceiling space. This hygrometer may be arranged not only above the nozzles 66N but also on other portion (for example, the upper surface of the sealing member) or may be provided separately from the installation member. Further, the first to fourth embodiments may include a hygrometer.

In the fifth embodiment, the control unit 28 stops the spraying when the humidity measured by the hygrometer reaches the target relative humidity. The present disclosure is not limited to this, and the control unit 28 may obtain the humidity from the hygrometer at the spraying end time and, when the humidity in the ceiling space is less than the target relative humidity, may spray additional chemical solution until the target relative humidity is achieved.

Various changes in form and details may be made to the examples above without departing from the spirit and scope of the claims and their equivalents. The examples are for the sake of description only, and not for purposes of limitation. Descriptions of features in each example are to be considered as being applicable to similar features or aspects in other examples. Suitable results may be achieved if sequences are performed in a different order, and/or if components in a described system, architecture, device, or circuitry are combined differently, and/or replaced or supplemented by other components or their equivalents. The scope of the disclosure is not defined by the detailed description, but by the claims and their equivalents. All variations within the scope of the claims and their equivalents are included in the disclosure.

What is claimed is:

1. A disinfection apparatus comprising: an installation member, wherein the installation member includes: a panel member configured to seal a hole located in a ceiling; a nozzle configured to be placed in a ceiling space through the hole and spray a chemical solution to disinfect the ceiling space; a mount member configured to place the nozzle above the panel member, the mount member being extendable and retractable in a length of the mount member to determine a position of the nozzle in an up-down direction; and a fixing member configured to maintain a state in which the panel member seals the hole, the fixing member includes a support, the support is extendable in a length of the support to elevate the fixing member and is retractable in the length of the support to lower the fixing member, and the support is extendable to stand on a floor and press the ceiling so as to fix the panel member.

2. The disinfection apparatus according to claim 1, wherein
the mount member is configured to be coupled to the panel member, and
the panel member is configured to support the nozzle.

3. The disinfection apparatus according to claim 1, wherein
the panel member has a shape corresponding to a grid of a grid ceiling, and
the fixing member is configured to fix the panel member by pressing the panel member against the grid.

4. The disinfection apparatus according to claim 2, wherein
the panel member has a shape corresponding to a grid of a grid ceiling, and
the fixing member is configured to fix the panel member by pressing the panel member against the grid.

5. The disinfection apparatus according to claim 1, wherein the fixing member includes an engagement portion configured to bring the panel member into engagement with a ceiling component, which forms the ceiling, or a ceiling access opening component, which forms a ceiling access opening located in the ceiling.

6. The disinfection apparatus according to claim 2, wherein the fixing member includes an engagement portion configured to bring the panel member into engagement with a ceiling component, which forms the ceiling, or a ceiling access opening component, which forms a ceiling access opening located in the ceiling.

7. The disinfection apparatus according to claim 1, further comprising:
a hygrometer configured to measure a humidity in the ceiling space; and
circuitry configured to control spraying from the nozzle,
wherein the circuitry is configured to perform spraying of the chemical solution until the humidity measured by the hygrometer reaches a target relative humidity.

8. The disinfection apparatus according to claim 2, further comprising:
a hygrometer configured to measure a humidity in the ceiling space; and
circuitry configured to control spraying from the nozzle,
wherein the circuitry is configured to perform spraying of the chemical solution until the humidity measured by the hygrometer reaches a target relative humidity.

9. The disinfection apparatus according to claim 3, further comprising:
a hygrometer configured to measure a humidity in the ceiling space; and
circuitry configured to control spraying from the nozzle,
wherein the circuitry is configured to perform spraying of the chemical solution until the humidity measured by the hygrometer reaches a target relative humidity.

10. The disinfection apparatus according to claim 4, further comprising:
a hygrometer configured to measure a humidity in the ceiling space; and
circuitry configured to control spraying from the nozzle,
wherein the circuitry is configured to perform spraying of the chemical solution until the humidity measured by the hygrometer reaches a target relative humidity.

11. The disinfection apparatus according to claim 1, wherein
the mount member is provided on an upper surface of the panel member,
the nozzle is attached to the mount member, and
the fixing member is provided on a lower surface of the panel member.

12. The disinfection apparatus according to claim 1, wherein the mount member is extendable and retractable in the length of the mount member and the support is extendable and retractable in the length of the support, independently.

* * * * *